United States Patent
Aguadisch et al.

[11] Patent Number: 6,120,791
[45] Date of Patent: Sep. 19, 2000

[54] METHODS FOR MAKING CONTROLLED RELEASE DEVICES FOR PHARMACEUTICALS

[75] Inventors: Louis Michel Jacques Aguadisch, Valbonne; Patrick Robert Peignot, Roquefort Les Pins; Alain Etienne, Toulouse; Frederic Jean_Claude Goutte, Schwoben, all of France

[73] Assignee: Dow Corning France S.A., Sophia Antipolis, France

[21] Appl. No.: 09/113,636

[22] Filed: Jul. 10, 1998

[30] Foreign Application Priority Data

Jul. 17, 1997 [FR] France .................................. 97-09089

[51] Int. Cl.$^7$ ...................................... A61K 9/00
[52] U.S. Cl. .......................... 424/443; 424/400; 264/477; 264/566; 264/573
[58] Field of Search ...................... 424/400, 468, 424/443, 502, 485, 43; 264/477, 566, 573

[56] References Cited

FOREIGN PATENT DOCUMENTS

| | | |
|---|---|---|
| WO91/10425 | 7/1991 | European Pat. Off. . |
| 0791354 | 8/1997 | European Pat. Off. . |
| 2753086 | 3/1998 | France . |
| WO 91/10425 | 7/1991 | WIPO . |
| WO 97/15293 | 5/1997 | WIPO . |
| WO 98/10755 | 3/1998 | WIPO .............................. A61K 9/48 |

*Primary Examiner*—Thurman K. Page
*Assistant Examiner*—William E. Benston, Jr.
*Attorney, Agent, or Firm*—Roger E. Gobrogge

[57] ABSTRACT

The invention relates to a process for making a controlled release device suitable for introduction into a human or animal body. The process comprises coextruding a continuous external body comprising a silicone elastomer and one or more elements comprising a synthetic pharmaceutical agent within the continuous external body.

12 Claims, 2 Drawing Sheets

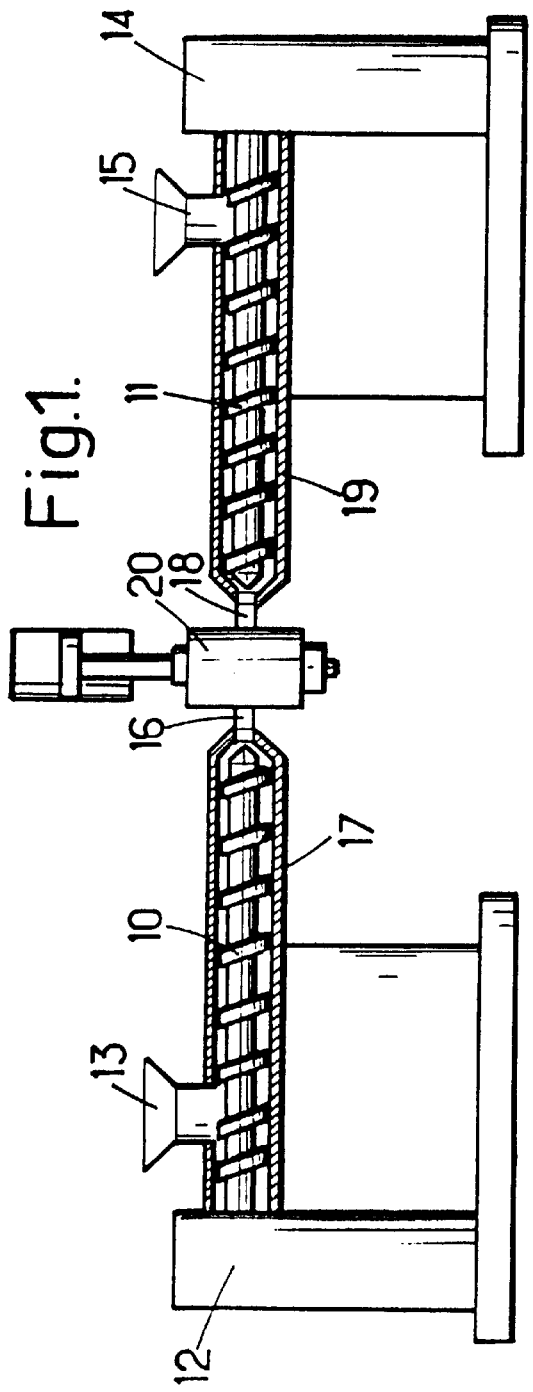
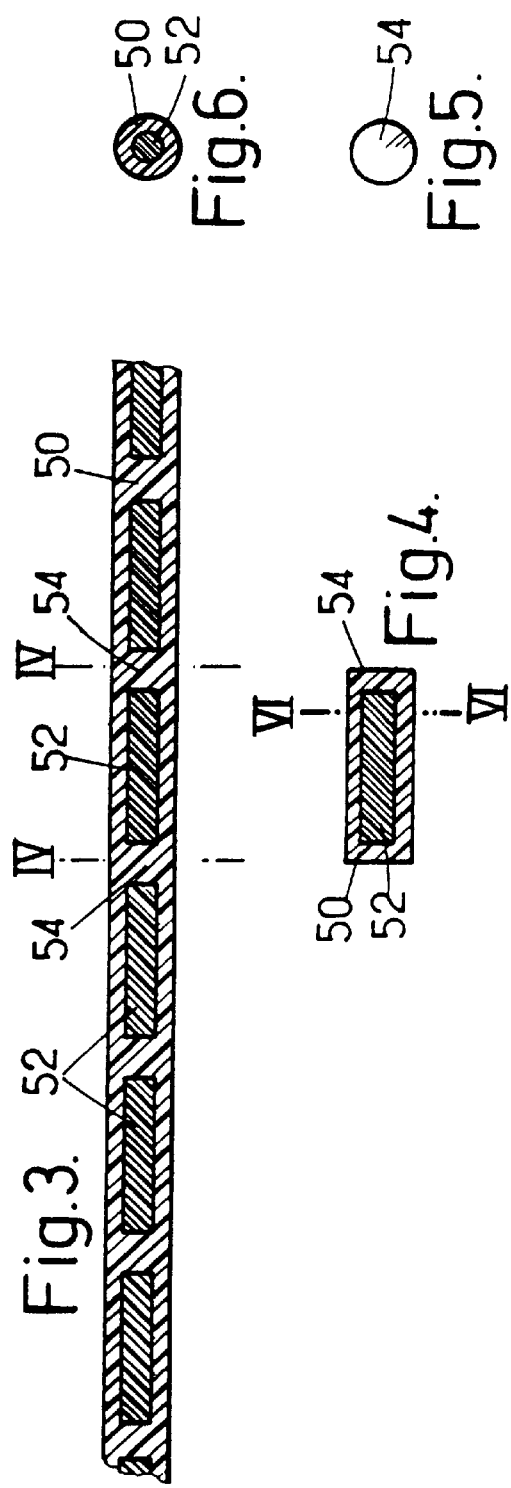

METHODS FOR MAKING CONTROLLED RELEASE DEVICES FOR PHARMACEUTICALS

BACKGROUND OF THE INVENTION

The present invention relates to methods for making controlled release devices for delivering synthetic pharmaceuticals to humans and animals and to the devices produced by these methods.

Numerous methods for making devices for the controlled release of pharmaceutical preparations into the human or animal body have been proposed. For example, it has been proposed to manufacture this type of device by using a tube of silicone elastomer, sealing one end of the tube with a composition of curable silicone, charging the tube with a composition containing the synthetic pharmaceutical agent, sealing the open end of the tube with a composition of curable silicone and then curing the silicone composition. Although the devices produced by this process are efficient as vehicles for administering phamaceutical agents, the method used to make them involves a large expenditure of time and effort.

We have now discovered that consistently high quality devices for the controlled release administration of synthetic pharmaceuticals can be prepared by a co-extrusion process.

SUMMARY OF THE INVENTION

In one of its aspects, the present invention provides a co-extrusion process for the production of a controlled release device comprising:

(i) supplying a first nozzle orifice of an extrusion apparatus with a first composition and continuously extruding said first composition through said first nozzle orifice to form a continuous extrudate body, said first composition comprising a silicone;

(ii) simultaneous with the extrusion of said first composition, supplying a second nozzle orifice situated inside the first nozzle orifice with a second composition and extruding said second composition through said second orifice; and (iii) periodically restricting the extrusion of said second composition so that at least one element of the second composition having a predetermined volume is extruded within the continuous extrudate body, the second composition comprising a synthetic pharmaceutical agent.

In the process of the invention, extrusion of the second composition can be controlled as required by the frequency and degree of restriction applied. Thus, the volume of the elements can be controlled as required and, when the restriction is applied, the extrusion of the compositions can be continued at a lesser rate or can be interrupted. Preferably the elements can be isolated from each other in the body of the device (i.e., separated) by portions of material of the first composition extending through the cross section of the article.

Controlled release devices in accordance with the invention are suitable for introduction into the human or animal body. They comprise an external body of a first silicone-containing composition in which one or more elements of the second composition are enclosed. They can be made by cutting an extrudate produced by a process of the invention into segments containing one or more elements of the second composition. The ends of the device can be closed as required by portions of the extruded material of the first composition. The extrudate can be cut into segments at any required stage of the process.

The specific materials used in the process of the invention and the configuration selected for the elements depend on the characteristics of the synthetic pharmaceutical agent and on the rate of release which is required.

BRIEF DESCRIPTION OF THE DRAWINGS

FIG. 1 is a view of an apparatus used in the illustrative process;

FIG. 3 is a diagram of a longitudinal section of an example extrudate article formed in the execution of the first illustrative process;

FIG. 4 is a larger scale view of the illustrative device formed by cutting the article of FIG. 4 along the lines IV—IV;

FIG. 5 is an end view of the first illustrative device;

FIG. 6 is a sectional view through the line VI—VI of FIG. 4.

DETAILED DESCRIPTION OF THE INVENTION

Figure 2:
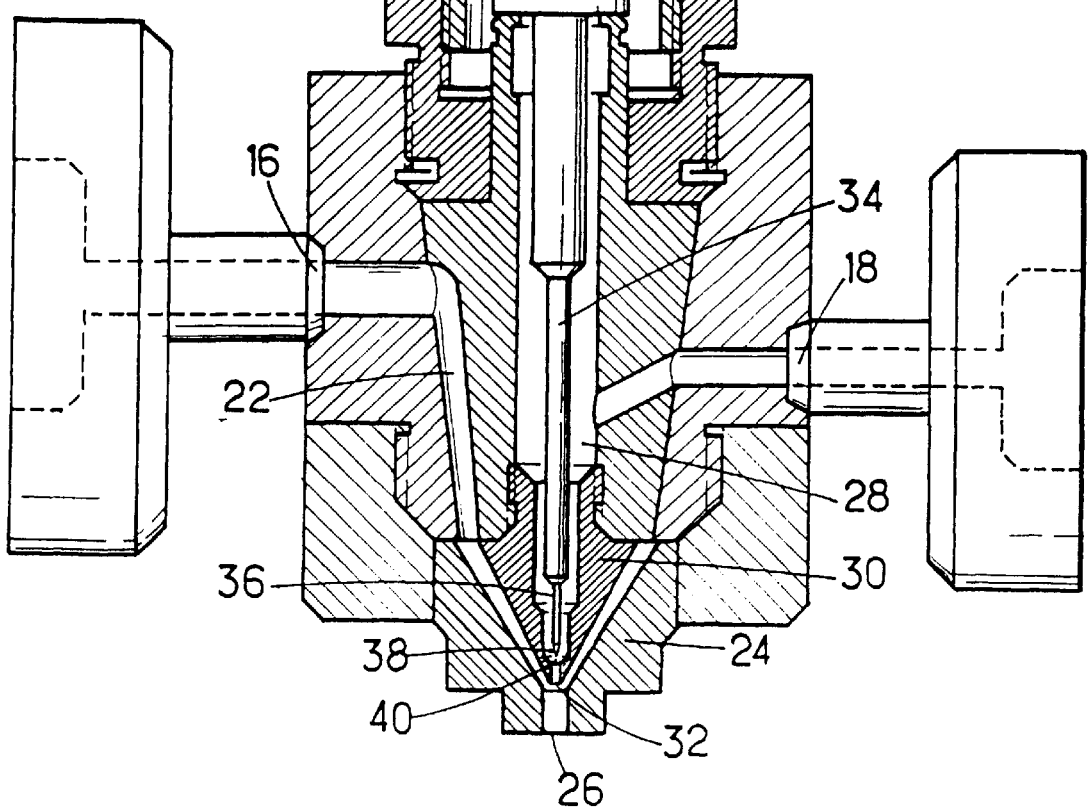
FIG. 2 is a diagrammatic sectional view of an extrusion head system of the apparatus used in the execution of the illustrative process.

The first composition which is used in the present invention to produce the continuous extrudate body generally comprises a silicone-containing material. The silicone may be used alone or it may be used in combination with, or as a copolymer of, any other material which is recognised as suitable for implantation in the human or animal body. These materials include, for example, polymers and copolymers of unsaturated monomers such as polymethacrylates, polyvinyl chloride, polyethylene, polyacrylonitrile, polyvinyl acetate and polybutadiene, polyesters, polyamides, polyurethanes, and esters of cellulose.

The first composition preferably comprises organosilicone materials capable of curing to an elastomeric state. This curing can take place at ambient or high temperatures and it may require a curing agent and/or a catalyst. Likewise, the organosilicone materials may cure slowly at ambient temperature and have a higher cure rate at high temperatures (e.g., 70 to 110° C.).

The first composition also preferably comprises organosilicone materials which cure without the production of volatile by-products. Such volatile by-products can cause voids in the device which are generally undesirable unless suitably controlled. In addition, the absence of volatile by-products simplifies the manufacturing process and the compositions undergo little or no volume change during curing.

The organosilicone materials used in the first composition are also preferably such that the composition is extrudable and yet capable of retaining its shape (i.e., resistant to flow) after extrusion and before cure has fully developed.

Based on these criteria, the most preferred first compositions often comprise organosilicone materials which cure by a hydrosilylation reaction. This reaction occurs at relatively low temperatures which may be desirable when certain synthetic pharmaceutical agents are used.

Organosilicone materials which cure by the hydrosilylation reaction comprise one or more organopolysiloxanes which contain at least two groups having aliphatic unsaturation bonded to silicon, one or more organosilicone compounds having at least two atoms of hydrogen bonded to silicon and a catalyst which activates the reaction between the unsaturated groups and the hydrogen atoms bonded to the silicon.

The organopolysiloxane having aliphatic unsaturation used in a composition which cures by hydrosilylation is typically a polysiloxane of relatively high molecular weight (e.g., those having a gum consistency) and which comprises structures of the general formula $Q_aQ'SiO_{(3-a)/2}$ and $Q_bSiO_{(4-b)/2}$, in which Q represents a monovalent hydrocarbon group having not more than 8 carbon atoms such as a methyl group or a phenyl group or a monovalent hydrocarbon group having not more than 8 carbon atoms substituted with atoms such as silicon, oxygen, nitrogen, halogens, sulfur and the like, and Q' represents an ethylenically unsaturated organic group, preferably a vinyl, allyl or hexenyl group, the value of $a$ is 1 or 2, and the value of b is 0, 1, 2, or 3. Preferably, at least 80% of the Q groups are methyl groups.

The organosilicone compound having Si—H bonds used in a composition which cures by hydrosilylation is typically an organohydrogensiloxane which has a maximum viscosity of approximately 50 mm$^2$/s and which contains at least two hydrogen atoms bonded to silicon per molecule. The other substituents bonded to the silicon in such a compound are monovalent hydrocarbon groups having no more than 8 carbon atoms and are preferably methyl groups.

The catalyst used in a composition which cures by hydrosilylation is typically a compound or complex containing platinum or rhodium such as chloroplatinic acid, platinum acetylacetonate, a complex of platinum halides with unsaturated compounds such as ethylene, propylene, organovinylsiloxanes and styrene and methyldiplatinum.

A composition which cures by hydrosilylation may also contain a catalyst inhibitor, for example, an acetylene compound such as an acetylenically unsaturated secondary or tertiary alcohol. An example of such an inhibitor is ethynylcyclohexanol.

These first compositions which cure by the hydrosilylation reaction preferably cure in a short period of time at the operating temperatures of the extrusion device, e.g., 15° C. to 110° C. Compositions of this type are known in the art (see, for example, the descriptions of British patents Nos. 1 090 122, 1 141 868 and 1 409 223) and are commercially available.

Alternative organosilicone materials which can be used in the first composition include elastomer-forming silicone compositions comprising organopolysiloxanes having hydroxyl groups bonded to silicon which can be cured by the addition of a curing agent and a condensation catalyst. In these compositions, the organopolysiloxane is generally a polydiorganosiloxane having silanol terminal groups. The curing agent may be, for example, an alkoxysilane or an alkyl polysilicate such as methyltrimethoxysilane or ethyl polysilicate, or it may be an alkylhydrogenpolysiloxane such as a polymethylhydrogenosiloxane. Various catalysts may be used including, for example, organometallic compounds such as stannous octoate, dibutyl tin dilaurate, alkyl titanates and titanium chelates. These elastomer forming compositions are also known in the art and have been described, for example, in British patents Nos. 841 825, 844 128, 957 255 and 962 061.

Other suitable silicone materials to be used in the first compositions include those which contain peroxides. Such materials can generate free radicals when heated or irradiated and these free radicals, in turn, cause the desired curing.

The first composition may also contain other ingredients such as materials which increase the permeability of body fluids, materials capable of influencing the rate of delivery of the synthetic pharmaceutical agent, plasticizers, fillers (which may, for example, be opaque to X-rays or to other radiation employed for diagnostic purposes), excipients used in pharmacy and compounds intended to act as pH buffers influencing the immediate environment inside and outside the device when it is in an aqueous medium.

Examples of materials which increase the permeability of body fluids and which can be used in the first composition to produce the body are those described and claimed in EP-A-425 154, the entire disclosure of which is hereby incorporated by reference. These include hydrophilic constituents comprising an organic hydrophilic material having two, or advantageously three or more, hydroxyl groups per molecule selected from liquid polyethylene glycols having a molecular weight in the range of 100 to 600, propylene glycol, glycerol, sorbitol and mannitol. Also included are modulating constituents which serves to modulate the expulsion of the synthetic pharmaceutical agent and which may be selected from hydrophilic constituent having two, or more, hydroxyl groups per molecule, and hydrophilic polymers which swell in an aqueous medium including cellulose materials, for example, cellulose and cellulose derivatives, such as carboxymethylcellulose, sodium carboxymethylcellulose whether reticulated or not, hydroxypropylcellulose and acetylated chitin. These hydrophilic materials and hydrophilic polymers serve to modify the release characteristics of the vehicle and to modulate the release in various ways. The material used is selected depending on the required characteristics of the element and on the required release profile in the site selected for the element.

In an alternative embodiment of the invention, the first composition may also comprise a composition containing a synthetic pharmaceutical agent as described hereinafter. If desired, the synthetic pharmaceutical agent in the first composition according to this embodiment of the invention can be continuous or intermittent (i.e., the synthetic pharmaceutical agent in the continuous extrudate body can be continuous or intermittent). Obviously, the synthetic pharmaceutical agent in the first and second compositions can be coordinated as desired.

The first composition can be extruded at ambient temperature or at high temperature and can solidify or cure after extrusion or, alternatively, they may require an additional cure step. If curing is required, it may be effected or accelerated in any suitable manner such as, for example, by the application of heat and/or with the assistance of curing agents. Heating could be accomplished, for example, by depositing the extrudate leaving the nozzle orifices onto a conveyor belt and passing it into an oven at a temperature which will not degrade the synthetic pharmaceutical agent.

The second composition used in the present invention to produce the elements comprises a synthetic pharmaceutical agent. The expression "synthetic pharmaceutical agent" as used herein means a therapeutic or diagnostic agent used to treat the human or animal body. Examples of these agents comprise those which are intended for release into body fluids by diffusion, for example, by passing through the bloodstream. These may include, for example, organic or mineral substances which have pharmaceutical activity and for which it is useful to administer in small doses over long periods of time.

The synthetic pharmaceutical agent may be selected in accordance with normal pharmaceutical practice and it normally has a pH adapted to the conditions prevalent in the region of the body in which it is to be released. If necessary, the pH of the substance may be buffered in order to preserve its activity.

The synthetic pharmaceutical agents which may be used can comprise, for example, organic and mineral agents which act on the central nervous system, agents which have contraceptive, hormone replacement, cardio-vascular and ophthalmic activity and antiparasitic, antifungal, antibacterial and antiviral agents. Examples include antibiotics, antiseptics, antiinflammatory agents, hormones, anticancer agents, smoking cessation agents, cardiovasculars, $H_2$ blockers, bronchodilators, analgesics, antiarrythmics, antihistamines, alpha blockers, beta blockers, ACE inhibitors, diuretics, antiaggregants, sedatives, tranquillisers, anticonvulsants, anticoagulants, vitamins, agents for treating gastric and duodenal ulcers, proteolytic enzymes, healing factors, cell growth nutrients, peptides and others. Specific examples of suitable synthetic pharmaceutical agents include penicillins, cephalosporins, tetracyclines, macrolides, epinephrine, amphetamines, aspirin, barbiturates, catecholamines, benzodiazepine, thiopental, codeine, morphine, procaine, lidocaine, sulphonamides, ticonazole, perbuterol, furosamide, prazosin, prostaglandins, salbutamol, indomethacine, diclofenac, glafenine, dipyridamole, and theophylline.

The concentration of the synthetic pharmaceutical agent used, the volume of the device and the size of the body of the device are selected so as to offer the required rate of release of the synthetic pharmaceutical agent or agents and the required duration of useful life of the device, i.e., the time during which the device is capable of releasing the synthetic pharmaceutical agent at the required rate.

The second composition may be in the form of a liquid, a solid, or a gel. The synthetic pharmaceutical agent can be used in an undiluted form or it can be diluted in an appropriate diluent. In an alternative embodiment of the invention, the synthetic pharmaceutical agent may be present in the second composition in combination with a support material, which support material may be a solid, liquid or gel and which may be cured as required. The preferred support material herein is a silicone, provided the second composition contains a maximum of approximately 40% by weight of the synthetic pharmaceutical agent. If desired, this silicone may be one of the silicone materials used to make the first composition and it may be cured as required. Where a larger charge of the synthetic pharmaceutical agent is necessary, the support material can be any material which is extrudable (e.g., from a liquid to a gum) and which is inert to the synthetic pharmaceutical agent.

If the synthetic pharmaceutical agent is to be incorporated in a silicone support material to form the second composition, it is done in accordance with conventional processes known in the art. For example, the synthetic pharmaceutical agent may be mixed with the silicone composition or in a part of its formulation.

The second composition may also contain other ingredients such as materials which increase the permeability of body fluids, materials capable of influencing the rate of delivery of the synthetic pharmaceutical agent, plasticizers, fillers (which may, for example, be opaque to X-rays or to other radiation employed for diagnostic purposes), excipients used in pharmacy and compounds intended to act as pH buffers influencing the immediate environment inside and outside the device when it is in an aqueous medium.

In another of its aspects, the present invention provides a controlled release device suitable for introduction into the human or animal body, characterised by the fact that it comprises a continuous external body comprising a silicone elastomer composition in which is enclosed one or more elements of at least one second composition, at least one of the second compositions comprising a synthetic pharmaceutical agent, the continuous external body and the elements having been formed in a single extrusion step.

In yet another of its aspects, the present invention provides a controlled release device suitable for introduction into the human or animal body comprising a continuous external body comprising a silicone elastomer composition and a synthetic pharmaceutical agent in which is enclosed one or more elements of at least one second composition, at least one of the second compositions comprising a synthetic pharmaceutical agent as defined above, the continuous external body and the second composition having been formed in a single extrusion step. The first and second compositions in this aspect of the invention may contain the same synthetic pharmaceutical agent, but we prefer that they contain different synthetic pharmaceutical agents so as to permit simultaneous administration of different synthetic pharmaceutical agents at the same or different doses and by the same or different mechanisms.

In yet another of its aspects, the present invention provides an article comprising a string formed by coextruding a minimum of two compositions and comprising a continuous external body of a first composition comprising a silicone in which is enclosed two or more elements of one or more second compositions, at least one of these second compositions comprising a synthetic pharmaceutical agent as defined above.

In the process of the invention described hereinafter, the nozzle of the first extrusion apparatus surrounds and is in axial alignment with an outlet orifice for a second, element forming, composition. The intermittent distribution of the second composition from a extruder reservoir to the second outlet orifice is controlled by a suitable valve device such as a pneumatic needle valve which can be operated so as to allow or prevent the flow of the second composition according to the pre-established required time intervals. The flow rates of the first composition and the second composition towards the nozzle and the outlet orifice can be modified independently as required and the extrusion of the body and of the core can thus be controlled as required.

The following is a description to be read with reference to the attached drawings of processes for the production of articles and devices, each of which illustrates aspects of the invention. The parts and percentages are all expressed by weight unless otherwise specified.

The illustrative process is a co-extrusion process for the manufacture of articles (FIG. 3) consisting of a continuous external body of extrudate containing within it one or more elements of predetermined volume of a second composition. The process can be used to manufacture controlled release devices comprising an external body with at least one second composition within it (FIGS. 4 to 6) suitable for introduction into the human or animal body.

The apparatus which can be used in the present invention (FIG. 1) comprises two extrusion units (12, 14), each provided with a screw system (10, 11) to convey the composition supplied in a hopper (13, 15) along a cylinder (17, 19) mounted so as to deliver the composition to intake conduits (16, 18) (FIG. 2) of an extrusion head (20) of the apparatus under sufficient conditions of temperature and pressure to cause the extrusion of the composition through the extrusion head. The intake conduit (16) of the extrusion head (20) communicates with the chamber (22) and an associated nozzle (24). The nozzle (24) has a nozzle orifice (26).

The intake conduit (18) of the extrusion head (20) communicates with a chamber (28) and an associated nozzle (30). The nozzle (30) has a nozzle orifice (32) centred exactly above the first nozzle orifice (26). A valve (34) includes a first point (36) arranged in the second nozzle (30) and a neck in the form of a truncated cone (38) which can come to rest against a valve seat (40) provided in the upper part of the orifice (32) of the nozzle (30). A pneumatic means comprising a piston and cylinder system (42) is provided to operate the valve (34) so as to control the flow of the composition through the nozzle orifice (32). A threaded sleeve is mounted between the nozzles and the piston and cylinder system for the latter to be adjustable in the direction of the height of the valve so as to permit adjustment of the stroke of the piston and cylinder system and thus allow adjustment of the volume of composition delivered through the nozzle orifice (32). The operation of the piston and cylinder system to open and close the second orifice (32) is controlled by an electronic control means set so as to lift (as shown in FIG. 2) or lower the valve successively at pre-established time intervals. Thus, although the composition is continuously pushed to flow towards the nozzle (30) from the intake conduit (18), its flow through the extrusion head passing through the nozzle orifice (32) is periodically restricted by the valve (34), with the result that a series of elements of predetermined volume of the composition can be extruded through the nozzle orifice (32).

In the execution of the illustrative process, a first composition was supplied to the extruder (12) of the apparatus (FIG. 1) and extruded continuously under constant pressure (i.e., the screw (10) being set to operate at a constant rotational velocity) through the nozzle orifice (26) to form a continuous extrudate body (50 in FIG. 3). A second composition was supplied to the extruder (14) under constant pressure to be extruded through the nozzle orifice (32). The apparatus was operated as explained above so that a series of elements (52 in FIG. 3) of predetermined volume of the second composition has been extruded through the nozzle orifice (32) within the continuous body (50).

In the illustrative process, the flow of the second composition (i.e., the internal composition) was subject to successive total interruptions to produce a continuous article comprising a continuous external body (50) (FIG. 3) of the first composition in which was enclosed a series of elements (52) of the second composition separated by blank portions or stretches (54) of material of the first composition extending through the cross-section of the article.

The illustrative process also comprises the steps consisting of receiving the extrudate on a conveyor belt provided with a heating oven to harden the first composition and of dividing the article into sections, for example, by means of a knife at required positions, for example, cutting it in the middle of the blank stretches (54) as shown at IV—IV in FIG. 3. The cut may be made through adjacent blank stretches or through spaced apart blank stretches.

Using the illustrative process, controlled release devices can be made of various designs and configurations adapted for introduction into the human or animal body. The illustrative device shown in the attached drawings is an example of certain of these designs. Each comprises an external body (50) of a first composition in which is enclosed one or more elements (52) of a same or a different second composition. The illustrative device has a single element (52) of the second composition and the ends of the device are closed by portions of the extruded material of the first composition. A similar device may comprise several elements (52), the adjacent elements of the device being completely separated from each other by a portion of the material of the first composition which extends through the cross-section of the device.

Particular examples of the use of the first and second illustrative processes to produce devices for synthetic pharmaceutical agent delivery will now be described.

EXAMPLE 1

A first composition was formed by mixing a curable elastomer of medical quality, available commercially, comprising 62 parts of a polydimethylsiloxane terminated by dimethylvinylsilyl groups having a molecular weight of 700 000, 26 parts of silica, 5 parts of a dimethyl-methylvinylpolysiloxane terminated by dimethylvinylsilyl groups having a molecular weight of 700 000, 5 parts of a polydimethylsiloxane terminated by dimethylhydroxyl substituents having a molecular weight of 1100, 1 part of a dimethyl-methylhydrogenopolysiloxane having a molecular weight of 712 and 0.2 parts of a catalyst comprising a platinum complex.

A second composition was prepared from 20 parts of a micronized synthetic pharmaceutical agent, 14 parts of a polydimethylsiloxane of 0.001 $m^2/s$ (1000cSt) (PDMS), 1 part of barium sulphate and 65 parts of a hardenable elastomer of medical quality having a molecular weight of 700 000 and comprising 50 parts of a polydimethylsiloxane terminated by dimethylvinylsilyl groups, 34 parts of silica, 6 parts of a dimethyl-methylvinylpolysiloxane terminated by dimethylvinylsilyl groups with a molecular weight of 700 000, 8 parts of a polydimethylsiloxane terminated by dimethylhydroxyl substituents with a molecular weight of 1100, 1 part of a dimethyl-methylhydrogenopolysiloxane having a molecular weight of 712 and 0.2 parts of a catalyst comprising a platinum complex. The micronised synthetic pharmaceutical agent and the barium sulphate were mixed with PDMS using a mixer. The master mixture obtained was then incorporated in the elastomer using a two-cylinder mixer.

The first composition was extruded at a screw velocity of 13 rpm through the first nozzle orifice having a diameter of 2.20 mm to form the continuous extrudate body. The second composition was simultaneously extruded at a velocity of 9.5 rpm through the second nozzle orifice having a diameter of 0.5 mm.

The cycle of successive operations performed by the automatic pneumatic valve system adjusted to a piston stroke of 0.5 mm permitted periodic extrusion of the second composition for 0.65 seconds, interrupted by intervals of 0.40 seconds during which there was no flow of the second composition through the second nozzle orifice.

The continuous article obtained was heated by passing it in an oven system heated to 150° C. for 45 seconds with a synchronised conveyer belt in order to activate the cure of the composition. The resulting article was then cut in the middle of the blank stretches to form separated devices having the following dimensions:

| | |
|---|---|
| Total length | 40.00 mm |
| External diameter | 2.35 mm |
| Internal element: | |
| Length | 35.00 mm |
| Diameter | 1.30 mm |

EXAMPLE 2

Using the same formulation and the same apparatus as in Example 1, a article was extruded with application of the following conditions:

Extrusion speed of the first composition through the first nozzle orifice: 11 rpm.

Extrusion speed of the second composition through the second nozzle orifice: 14 rpm.

Cycle of successive interruptions: the flow time was fixed at 0.50 seconds and the supply interruption time was fixed at 0.50 seconds.

The conditions of hardening and treatment of the article were the same as in Example 1. Devices having the following dimensions were obtained:

| | |
|---|---|
| Total length | 40.00 mm |
| External diameter | 2.35 mm |
| Internal element: | |
| Length | 35.00 mm |
| Diameter | 1.70 mm |

EXAMPLE 3

A first composition comprising the same composition as that used as the second composition in Example 1 was formed.

A second composition was prepared from an non-curable formulation comprising 20 parts of a PDMS gum (plasticity 1.40–1.65 mm) and 80 parts of a micronised synthetic pharmaceutical agent. The two components were mixed together homogeneously using a mixer with a Z-shaped blade.

The first and second compositions were co-extruded as described in Examples 1 and 2 with application of the conditions indicated in Table 1 below. The resulting dimensions of the devices obtained are also shown in Table 1:

TABLE 1

| Extrusion speed | | | | |
|---|---|---|---|---|
| through the first nozzle orifice (diameter 2.20 mm) rpm | 36.00 | 44.00 | 55.00 | 45.00 |
| through the second nozzle orifice (diameter 1.00 mm) rpm | 7.20 | 13.80 | 13.80 | 8.60 |
| Cycle: flow (s) | 0.35 | 0.35 | 0.35 | 0.45 |
| closure (s) | 0.25 | 0.25 | 0.25 | 0.25 |
| Device dimensions | | | | |
| Total length (mm) | 37.00 | 34.00 | 43.00 | 35.00 |
| External diameter (mm) | 2.32 | 2.24 | 2.25 | 2.32 |
| Internal element (mm) | | | | |
| Length | 33.00 | 30.00 | 39.00 | 31.00 |
| Diameter | 1.56 | 1.43 | 1.48 | 1.23 |
| Wall thickness (mm) | 0.76 | 0.81 | 0.77 | 1.09 |

EXAMPLE 4

A first composition was formed by mixing a curable elastomer of medical quality using the same formulation as that used for the second composition in Example 1, but including 2 additional parts of a terpolymer of trimethylsiloxy end-blocked methylhydrogenopolysiloxane and silica. The second composition used was the same as that used in Example 3.

The first and second compositions were co-extruded as described in Examples 1 and 2 with application of the conditions indicated in Table 2 below the resulting dimensions of the devices are also shown in Table 2:

TABLE 2

| Extrusion speed | | | | |
|---|---|---|---|---|
| through the first nozzle orifice (diameter 2.20 mm) rpm | 47.00 | 47.00 | 35.00 | 28.00 |
| through the second nozzle orifice (diameter 1.00 mm) rpm | 9.50 | 13.30 | 13.30 | 14.30 |
| Cycle: flow (s) | 0.50 | 0.35 | 0.50 | 0.35 |
| closure (s) | 0.30 | 0.30 | 0.50 | 1.00 |
| Device dimensions | | | | |
| Total length (mm) | 37.00 | 36.00 | 40.00 | 38.00 |
| External diameter (mm) | 2.30 | 2.25 | 2.33 | 2.31 |
| Internal element (mm) | | | | |
| Length | 33.00 | 32.00 | 36.00 | 34.00 |
| Diameter | 1.35 | 1.51 | 1.73 | 1.61 |
| Wall thickness (mm) | 0.95 | 0.74 | 0.61 | 0.70 |

That which is claimed is:

1. A co-extrusion process for the production of a controlled release device comprising:

(i) supplying a first nozzle orifice of an extrusion apparatus with a first composition and continuously extruding said first composition through said first nozzle orifice to form a continuous extrudate body, said first composition comprising a silicone;

(ii) simultaneous with the extrusion of said first composition, supplying a second nozzle orifice situated inside the first nozzle orifice with a second composition and extruding said second composition through said second orifice; and (iii) periodically restricting the extrusion of said second composition so that at least one element of said second composition having a predetermined volume is extruded within the continuous extrudate body, the second composition comprising a synthetic pharmaceutical agent.

2. The process of claim 1 wherein the restriction of the extrusion of the second composition is such that at least two elements of the second composition are separated from each other in the continuous extrudate body.

3. The process of claim 2 wherein the first composition is extruded in such a manner that the elements are completely separated from each other by the first composition which extends through the cross-section of the device.

4. The process of claim 3 wherein the device is cut into sections at the area where the first composition extends through the cross-section of the article.

5. The process of claim 1 wherein the first composition is extruded in such a manner that the ends of the device are closed by the first composition which extends through its cross-section.

6. The process of claim 1 wherein the extruded device is cured.

7. The process of claim 1 wherein the synthetic pharmaceutical agent is such that it can be released into the body fluids by diffusion.

8. The process of claim 1 wherein the first composition contains a synthetic pharmaceutical agent.

9. A controlled release device suitable for introduction into the human or animal body, characterised by the fact that it comprises an continuous external body comprising a silicone elastomer composition and a synthetic pharmaceutical agent in which is enclosed one or more elements of at least one second composition, at least one of the second compositions comprising a synthetic pharmaceutical agent, the continuous external body and the elements having been formed in a single extrusion step.

10. The device of claim 9 wherein the ends of the device are closed by the silicone elastomer composition which forms the continuous external body.

11. The device of claim 9 wherein the synthetic pharmaceutical agent in the first composition and the synthetic pharmaceutical agent in the second composition are different.

12. A string of controlled release devices foamed by coextruding a minimum of two compositions, said string comprising a continuous external body of a first composition comprising a silicone in which is enclosed two or more elements of a second composition separated from each other by the first composition which extends through the cross-section of the device, said second compositions comprising a synthetic pharmaceutical agent.

* * * * *